United States Patent

Heymes et al.

[11] 4,396,618
[45] * Aug. 2, 1983

[54] ALKYLOXIMES OF 7-AMINO-THIAZOLYL-ACETAMIDO-CEPHALOSPORANIC ACIDS

[75] Inventors: Rene Heymes, Romainville; Andre Lutz, Strasbourg, both of France

[73] Assignee: Roussel Uclaf, Paris, France

[*] Notice: The portion of the term of this patent subsequent to May 1, 1996, has been disclaimed.

[21] Appl. No.: 94,196

[22] Filed: Nov. 14, 1979

Related U.S. Application Data

[60] Division of Ser. No. 796,315, May 12, 1977, Pat. No. 4,202,893, which is a continuation-in-part of Ser. No. 781,344, Mar. 25, 1977, abandoned.

[30] Foreign Application Priority Data

Mar. 25, 1976 [FR] France .................... 76 08690

[51] Int. Cl.³ .................. A61K 31/545; C07D 501/22
[52] U.S. Cl. ..................... 424/246; 544/22; 544/28
[58] Field of Search ............ 544/28, 22; 424/246

[56] References Cited

U.S. PATENT DOCUMENTS

| | | | |
|---|---|---|---|
| 4,098,888 | 7/1978 | Ochiai et al. | 544/27 |
| 4,152,432 | 5/1979 | Heymes et al. | 544/28 |
| 4,278,671 | 7/1981 | Ochiai et al. | 424/246 |
| 4,298,606 | 11/1981 | Ochiai et al. | 424/246 |

Primary Examiner—Paul M. Coughlan, Jr.
Attorney, Agent, or Firm—Hammond & Littell, Weissenberger and Muserlian

[57] ABSTRACT

Novel alkyloximes of 7-amino-thiazolyl-acetamide-cephalosporanic acids of the formula

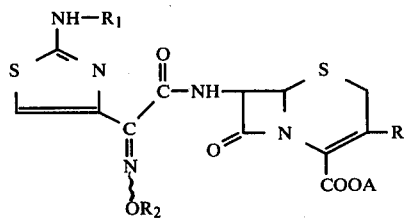

wherein R is selected from the group consisting of alkyl of 1 to 5 carbon atoms, cycloalkyl of 3 to 5 carbon atoms and —$CH_2$—SR', R' is selected from the group consisting of acyl of an alkanoic acid of 2 to 4 carbon atoms, 1-methyl-tetrazolyl and 2-methyl-1,3,4-thiadiazolyl, $R_1$ is selected from the group consisting of hydrogen and a group easily removeable by acid hydrolysis or hydrogenolysis, $R_2$ is selected from the group consisting of alkyl of 1 to 4 carbon atoms and alkenyl and alkynyl of 2 to 4 carbon atoms, A is selected from the group consisting of hydrogen, an alkali metal cation, an equivalent of an alkaline earth metal or magnesium, an organic amine base cation and an ester group easily removeable by acid hydrolysis or hydrogenolysis with the proviso that when $R_1$ is hydrogen, A is not an ester group easily removeable by hydrogenolysis or acid hydrolysis and the wavy line means that $OR_2$ is in one or the other of the two possible syn or anti isomeric positions having a very good antibiotic activity and novel processes and intermediates for their preparation.

8 Claims, No Drawings

ALKYLOXIMES OF 7-AMINO-THIAZOLYL-ACETAMIDO-CEPHALOSPORANIC ACIDS

PRIOR APPLICATION

This application is a division of U.S. application Ser. No. 796,315 filed May 12, 1977, now U.S. Pat. No. 4,202,893, which in turn is a continuation-in-part of our copending application Ser. No. 781,344 filed Mar. 25, 1977, now abandoned.

STATE OF THE ART

French Pat. No. 2,137,899 and No. 2,137,900 disclose antibiotic cephalosporin compounds of a different formula.

OBJECTS OF THE INVENTION

It is an object of the invention to provide the novel cephalosporanic acid derivatives of formula I.

It is another object of the invention to provide novel processes and novel intermediates for the preparation of compounds of formula I.

It is an additional object of the invention to provide novel antibiotic compositions and to provide a novel process for combatting bacterial infections in warm-blooded animals.

These and other objects and advantages of the invention will become obvious from the following detailed description.

THE INVENTION

The novel alkyloximes of 7-amino-thiazolyl-acetamido-cephalosporanic acid derivatives of the invention are comprised of compounds of the formula

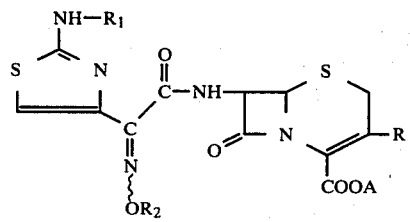

wherein R is selected from the group consisting of alkyl of 1 to 5 carbon atoms, cycloalkyl of 3 to 5 carbon atoms and —CH$_2$—SR', R' is selected from the group consisting of acyl of an alkanoic acid of 2 to 4 carbon atoms, 1-methyl-tetrazolyl and 2-methyl-1,3,4-thiadiazolyl, R$_1$ is selected from the group consisting of hydrogen and a group easily removeable by acid hydrolysis or hydrogenolysis, R$_2$ is selected from the group consisting of alkyl of 1 to 4 carbon atoms and alkenyl and alkynyl of 2 to 4 carbon atoms, A is selected from the group consisting of hydrogen, an alkali metal cation, an equivalent of an alkaline earth metal or magnesium, an organic amine base cation and an ester group easily removeable by acid hydrolysis or hydrogenolysis with the proviso that when R$_1$ is hydrogen, A is not an ester group easily removeable by hydrogenolysis or acid hydrolysis and the wavy line means that OR$_2$ is in one or the other of the two possible syn or anti isomeric positions.

Examples of the acids for the acyl groups of R$_1$ are acetic acid, propionic acid, n-butyric acid and isobutyric acid. Examples of alkyl and cycloalkyl groups for R are methyl, ethyl, propyl, isopropyl, butyl, isobutyl, tert.-butyl, pentyl, cyclopropyl, cyclobutyl and cyclopentyl.

Groups easily removeable by acid hydrolysis or hydrogenolysis for R$_1$ are well known in cephalosporan chemistry and examples of these groups are tert.-butoxy carbonyl, trityl, benzyl, dibenzyl, trichloroethyl, carbobenzyloxy, formyl, trichloroethoxycarbonyl and 2-tetrahydropyranyl. Examples of alkyl, alkenyl and alkynyl groups of R$_2$ are methyl, ethyl, propyl, isopropyl, butyl, sec-butyl, tert.-butyl, vinyl, propenyl, butenyl, ethynyl and propargyl.

Examples of groups of A are sodium, potassium, lithium, calcium, magnesium, organic bases such as trimethylamine, triethylamine, methylamine, propylamine, N,N-dimethylethanolamine, tris(hydroxymethyl)-amino methane, arginine or lysine and groups easily removeable by acid hydrolysis or hydrogenolysis such as benzhydryl, tert.-butyl, benzyl, p-methoxybenzyl and trichloroethyl.

The compounds of formula I may exist in the form of the syn isomer of the formula

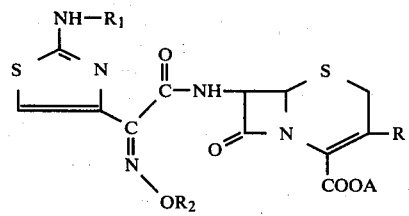

or in the form of the anti isomer of the formula

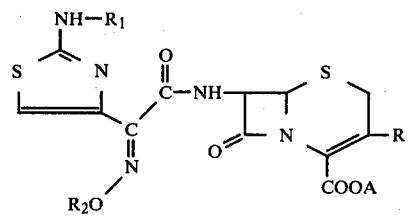

and the preferred compounds are those of formula I in the syn configuration for the —OR$_2$.

Among the preferred compounds of formula I are those wherein A is hydrogen, alkali metal cation, organic amine cation or equivalent of an alkaline earth metal or magnesium. The preferred groups for A which are easily removeable by acid hydrolysis or hydrogenolysis are benzhydryl, tert.-butyl, benzyl, p-methoxy benzyl and trichloroethyl. The preferred groups for R$_1$ which are easily removeable by acid hydrolysis or hydrogenolysis are tert.-butyoxy carbonyl, trityl, dibenzyl, trichloroethyl and carbobenzyloxy.

Another preferred group of compounds of formula I are those where R is —CH$_2$—S—R' and R' is acyl of an alkanoic acid of 2 to 4 carbon atoms, 1-methyl-tetrazolyl or 2-methyl-1,3,4-thiadiazolyl. Another preferred group are those of formula I wherein R is alkyl of 1 to 5 carbon atoms and cycloalkyl of 3 to 5 carbon atoms.

Another preferred group of formula I are those where R$_1$ is hydrogen or trityl, R$_2$ is methyl, R is —CH$_2$—S—R' and R' is acetyl, 2-methyl-1,3,4-thiadiazolyl or 1-methyl-tetrazolyl and A is hydrogen. Another preferred group of formula I is where R$_1$ is hydrogen, R$_2$ is methyl, R is —CH$_2$—S—R', R' is acetyl, 2-methyl-1,3,4-thiadiazolyl or 1-methyl-tetrazolyl and A is hydrogen, alkali metal, organic amine or equivalent of an alkaline earth metal or magnesium.

A further preferred group of formula I are those where R$_1$ is hydrogen or trityl, R$_2$ is methyl, R is methyl or isopropyl and A is hydrogen. Also preferred are compounds of formula I where R$_1$ is hydrogen, R$_2$ is methyl, R is —CH$_2$—S—R', R' is acyl of an alkanoic acid of 2 to 4 carbon atoms and A is hydrogen or an alkali metal.

Specific preferred compounds of formula I are 7-[{2-(2-amino-4-thiazolyl)-2-methoxyiminoacetyl}amino]-3-[(1-methyl-tetrazol-5-yl)-thiomethyl]-ceph-3-eme-4-carboxylic acid, 7-[{2-(2-amino-4-thiazolyl)-2-methoxyiminoacetyl{amino]-3-[(2-methyl-1,3,4-thiadiazol-5-yl)-thiomethyl]-ceph-3-eme-4-carboxylic acid, 3-acetyl-thiomethyl-7-[{2-(2-amino-4-thiazolyl)-2-methoxyiminoacetyl}amino]-ceph-3-eme-4-carboxylic acid, 7-[{2-(2-amino-4-thiazolyl)-2-methoxyiminoacetyl}-amino]-3-isopropyl-ceph-3-eme-4-carboxylic acid, 7-[{2-(2-amino-4-thiazolyl)-2-methoxyiminoacetyl}-amino]-3-methyl-ceph-3-eme-4-carboxylic acid, the syn isomer of 7-[{2-(2-amino-4-thiazolyl)-2-methoxyiminoacetyl}-amino]-3-[(1-methyl-tetrazol-5-yl)-thiomethyl]-ceph-3-eme-4-carboxylic acid, syn isomer of 7-[{2-(2-amino-4-thiazolyl)-2-methoxyiminoacetyl}-amino]-3-[(2-methyl-1,3,4-thiadiazol-5-yl)-thiomethyl]-ceph-3-eme-4-carboxylic acid, syn isomer of 3-acetyl-thiomethyl-7-[{2-(2-amino-4-thiazolyl)-2-methoxyiminoacetyl}amino]-ceph-3-eme-4-carboxylic acid, syn isomer of 7-[(2-(2-amino-4-thiazolyl)-2-methoxyiminoacetyl)amino]-3-isopropyl-ceph-3-eme-4-carboxylic acid, syn isomer of 7-[{2-(2-amino-4-thiazolyl)-2-methoxyiminoacetyl}amino]-3-methyl-ceph-3-eme-4-carboxylic acid, 3-acetylthiomethyl-7-[{2-(2-amino-4-thiazolyl)-2-methoxyiminoacetyl}amino]-ceph-3-eme-4-carboxylic acid prepared as in Example 6, syn isomer of sodium 7-[{2-(2-amino-4-thiazolyl)-2-methoxyiminoacetyl}amino]-3-[(2-methyl-1,3,4-thiadiazol-5-yl)-thiomethyl]-ceph-3-eme-4-carboxylate, syn isomer of sodium 7-[{2-(2-amino-4-thiazolyl)-2-methoxyiminoacetyl}amino]-3-[(1-methyl-tetrazol-5-yl)-thiomethyl]-ceph-3-eme-4-carboxylate, syn isomer of sodium 3-acetylthiomethyl-7-[{2-(2-amino-4-thiaziolyl)-2-methoxyiminoacetyl}amino]-ceph-3-eme-4-carboxylate and the syn isomer of crystalline sodium 3-acetylthiomethyl-7-[{2-amino-4-thiazolyl)-2-methoxyiminoacetyl}amino]-ceph-3-eme-4-carboxylate.

The products of formula I may exist as indicated before or in the form of compounds of the formula

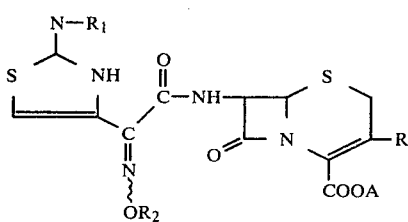

wherein R, R$_1$, R$_2$ and A have the above definitions.

The novel process of the invention for the preparation of the compounds of formula I comprises reacting a compound of the formula

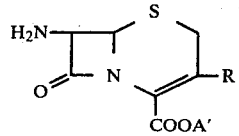

wherein R has the above definition and A' is selected from the group consisting of hydrogen and a group easily removeable by acid hydrolysis or hydrogenolysis with an acid of the formula

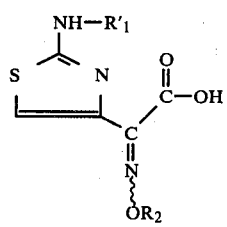

or a functional derivative thereof wherein R$_2$ has the above definition and R$_1$' is a group easily removeable by acid hydrolysis or hydrogenolysis to obtain a compound of the formula

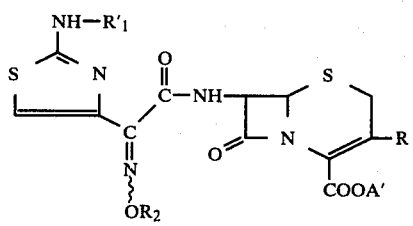

which may then be treated with an acid hydrolysis agent or an hydrogenolysis agent or both to obtain a compound of the formula

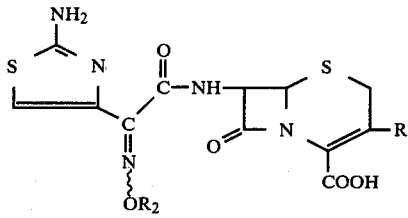

which may be salified to obtain the corresponding alkali metal, magnesium, alkaline earth metal or organic amine salt.

In a preferred mode of the process, the compound of formula II is reacted with a functional derivative of the acid of formula III such as the acid anhydride or the acid chloride or an anhydride formed in situ by reaction of the acid with isobutyl chloroformate or dicyclohexylcarbodiimide. Equally useful are other acid anhydrides formed in situ with other alkyl chloroformates, dialkylcarbodiimides or other dicycloalkylcarbodiimides or other acid halides as well as other acid derivatives such as acid azide, acid amide or active esters such as formed with hydroxy succinimide, p-nitrophenol or 2,4-dinitrophenol.

When the acid derivative is the acid chloride or anhydride with isobutyl chloroformate, the reaction is preferably effected in the presence of a basic agent such as an alkali metal carbonate or a tertiary organic amine such as N-methylmorpholine, pyridine or a trialkylamine such as triethylamine.

The transformation of the compounds of formula I' into the compounds of formula I" may be effected with an acid hydrolysis agent when $R_1'$ is a group easily removeable by acid hydrolysis and A' is hydrogen or a group easily removeable by acid hydrolysis. The product of formula I' may be treated with a hydrogenolysis agent when $R_1'$ is a group easily removeable by hydrogenolysis and A' is hydrogen or a group easily removeable by hydrogenolysis. The products of formula I' may be treated with an acid hydrolysis agent and a hydrogenolysis agent when one of $R_1'$ or A' is a group easily removeable by acid hydrolysis and the other is a group easily removeable by hydrogenolysis.

The acid hydrolysis agent for reaction with the products of formula I' may be formic acid, acetic acid or trifluoroacetic acid and they may be used as anhydrous or in aqueous solution. Equally useful is the zinc-acetic acid system. When the group to be removed is trityl or tert.-butoxycarbonyl for $R_1'$ or benzhydryl, tert.-butyl or p-methoxybenzyl for A', the acid hydrolysis agent is preferably anhydrous trifluoroacetic acid or aqueous formic acid or acetic acid. The zinc-acetic acid system is preferably used when $R_1'$ and A' are trichloroethyl. When $R_1'$ is dibenzyl or carbobenzyloxy or $R_1'$ and A' are benzyl, the hydrogenolysis agent is preferably hydrogen in the presence of a catalyst.

The compounds of formula I' or I" may be salified by known methods such as reacting the acid with an inorganic base such as sodium hydroxide, potassium hydroxide or sodium bicarbonate or with a salt of a substituted or non-substituted aliphatic carboxylic acid such as diethylacetic acid, ethylhexanoic acid and preferably acetic acid with the sodium salts of the acids being preferred. The salification may also be effected with an organic base such as triethylamine or diethylamine.

For the preparation of the salts, the free acids or the solvates of the free acids may be used as the starting material and the reaction is preferably effected in the presence of one or more solvents such as water, ether, methanol, ethanol and/or acetone. The salts will be obtained in crystalline or amorphous form depending upon the reaction conditions. The crystalline salts are preferably obtained by reacting the free acids with the salts of aliphatic carboxylic acids, preferably sodium acetate. For the preparation of a sodium salt, the reaction is effected in an appropriate organic solvent such as methanol containing small amounts of water.

The invention especially has for its object a process for the preparation of compounds of formula I wherein —$OR_2$ is in the syn position in which case the products of formula III have the group —$OR_2$ in the syn position.

In a variation of the process of the invention to produce a compound of formula I", a salt of a compound of formula I' wherein $R_1'$ is a group easily removeable by acid hydrolysis is treated with an acid to form a compound of formula I" or a salt of a compound of formula I' wherein $R_1'$ is a group easily removeable by hydrogenolysis is treated with a hydrogenolysis agent to obtain a salt of a compound of formula I".

The acid hydrolysis agent used in the said process is preferably formic acid but also useful are acetic acid or trifluoroacetic acid. The acid may be employed in the anhydrous form or in aqueous solution. The hydrogenolysis agent is preferably hydrogen in the presence of a hydrogenation catalyst.

In another variation of the process of the invention for the preparation of formula I", a compound of formula II is reacted with an acid of the formula

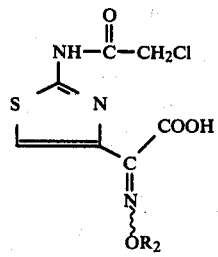

or a functional derivative thereof wherein $R_2$ has the above definition to obtain a compound of the formula

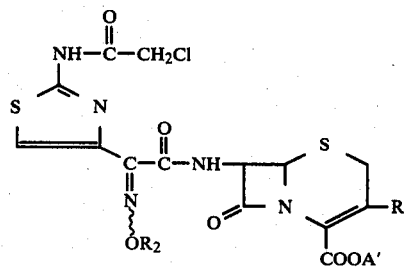

and reacting the latter with thiourea and then with an acid hydrolysis agent or a hydrogenolysis agent depending upon the value of A' to obtain a compound of formula I".

The reaction of the compound of formula II with the acid of formula $III_A$ is effected under the same conditions as the reaction of the compound of formula II with the acid of formula III discussed above. The reaction with thiourea and the compound of formula VI is preferably effected in neutral or acid conditions and this kind of reaction is described by Masaki [J.A.C.S., Vol. 90 (1968), p. 4508].

A process of the invention for the preparation of a compound of the formula

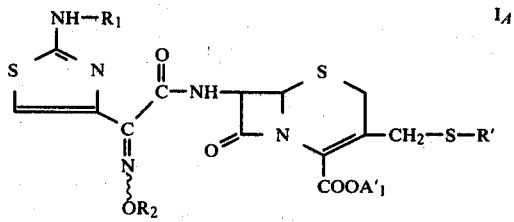

wherein $A_1'$ is selected from the group consisting of hydrogen, alkali metal, alkaline earth metal, magnesium or an organic amine base and $R_1$, $R_2$ and R' have the above definition comprises reacting a compound of the formula

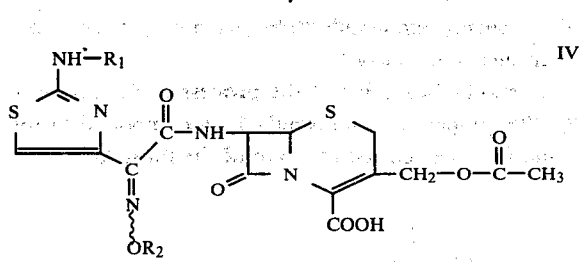

with a compound of the formula

R′-SH to obtain a compound of the formula

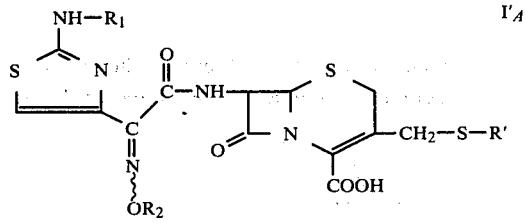

which may be salified to obtain a compound of formula I$_A$ wherein A$_1'$ is alkali metal, alkaline earth metal, magnesium or an organic amine base.

The reaction of a compound of formula V with a compound of formula IV is preferably effected in a water-acetone mixture but equally useful are other aqueous solvents such as water-dioxane, water-ethanol or water-tetrahydrofuran. The reaction is preferably effected in the presence of buffering agent to keep the pH of the medium slightly acidic such as a mixture of sodium acid phosphate-sodium bicarbonate but may also be effected without buffering agents. The salification can be effected by the known methods discussed above.

The invention has especially for its object the preparation of compounds of formula I$_A$ with the —OR$_2$ group in the syn form by using the products of formula IV with the —OR$_2$ group in the syn position.

The novel antibiotic compositions of the invention are comprised of an antibiotically effective amount of at least one compound of formula I and an inert pharmaceutical carrier or excipient. The compositions may be liquids or solids in the usual form such as tablets, dragees, gelules, granules, suppositories, injectable solutions or suspensions, pomades, creams, gels, etc.

Examples of suitable excipients are those usually used such as talc, arabic gum, lactose, starch, magnesium stearate, cacao butter, aqueous and non-aqueous vehicles, fatty bodies of animal or vegetable origin, paraffinic derivatives, glycols, preservatives, diverse wetting agents, dispersants or emulsifiers.

The compositions of the invention have a very good antibiotic activity against gram positive bacteria such as staphylococcus, streptococcus and especially penicillin-resistant staphylococcus and against gram negative bacteria such as coliform bacteria, Klebsiella, Salmonella and Proteus.

The compositions are therefore useful in the treatment of germ sensitive infections and particularly those of staphylococcia such as staphylococcal septicemia, staphylococcia malignant on the face or skin, pyodermatitis, septic or suppurantes sores, anthrax, phlegmons, eresipels, acute primitive or post-grip staphylococcia, bronchopneumonia or pulmonary suppurations. They are equally useful for the treatment of collibacillosis and associated infections, infections of Proteus, Klebsiella and Salmonella and other infections caused by gram negative bacteria.

Among the compositions of the invention are those wherein A is hydrogen, alkali metal cation, organic amine cation or equivalent of an alkaline earth metal or magnesium. The preferred groups for A which are easily removeable by acid hydrolysis or hydrogenolysis are benzhydryl, tert.-butyl, benzyl, p-methoxy benzyl and trichloroethyl. The preferred groups for R$_1$ which are easily removeable by acid hydrolysis or hydrogenolysis are tert.-butoxycarbonyl, trityl, dibenzyl, trichloroethyl and carbobenzyloxy.

Another preferred group of compositions of the invention are those where R is —CH$_2$—S—R′ and R′ is acyl of an alkanoic acid of 2 to 4 carbon atoms, 1-methyl-tetrazolyl or 2-methyl-1,3,4-thiadiazolyl. Another preferred group of compositions are those wherein R is alkyl of 1 to 5 carbon atoms and cycloalkyl of 3 to 5 carbon atoms.

Another preferred groups of compositions are those where R$_1$ is hydrogen or trityl, R$_2$ is methyl, R is —CH$_2$—S—R′ and R′ is acetyl, 2-methyl-1,3,4-thiadiazolyl or 1-methyl-tetrazolyl and A is hydrogen. Another preferred group of compositions are those where R$_1$ is hydrogen, R$_2$ is methyl, R is —CH$_2$—S—R′, R′ is acetyl, 2-methyl-1,3,4-thiadiazolyl or 1-methyl-tetrazolyl and A is hydrogen, alkali metal, organic amine or equivalent of an alkaline earth metal or magnesium.

A further preferred composition of the invention are those where R$_1$ is hydrogen or trityl, R$_2$ is methyl, R is methyl or isopropyl and A is hydrogen. Also preferred are compounds of formula I where R$_1$ is hydrogen, R$_2$ is methyl, R is —CH$_2$—S—R′, R′ is acyl of an alkanoic acid of 2 to 4 carbon atoms and A is hydrogen or an alkali metal.

Particularly preferred are compositions as described above, wherein the group OR$_2$ in the formula I is in the syn position.

Specific preferred compounds for the composition are 7-[{2-(2-amino-4-thiazolyl)-2-methoxyiminoacetyl}-amino]-3-[(1-methyl-tetrazol-5-yl)-thiomethyl]-ceph-3-eme-4-carboxylic acid, 7-[{2-(2-amino-4-thiazolyl)-2-methoxyiminoacetyl}amino]-3-[(2-methyl-1,3,4-thiadiazol-5-yl)-thiomethyl]-ceph-3-eme-4-carboxylic acid, 3-acetylthiomethyl-7-[{2-(2-amino-4-thiazolyl)-2-methoxyiminoacetyl}amino]-ceph-3-eme-4-carboxylic acid, 7-[{2-(2-amino-4-thiazolyl)-2-methoxyiminoacetyl}amino]-3-isopropyl-ceph-3-eme-4-carboxylic acid, 7-[{2-(2-amino-4-thiazolyl)-2-methoxyiminoacetyl}amino]-3-methyl-ceph-3-eme-4-carboxylic acid, the syn isomer of 7-[{2-(2-amino-4-thiazolyl)-2-methoxyiminoacetyl}-amino]-3-[(1-methyltetrazol-5-yl)-thiomethyl]-ceph-3-eme-4-carboxylic acid, syn isomer of 7-[{2-(2-amino-4-thiazolyl)-2-methoxyiminoacetyl}amino]-3-[(2-methyl-1,3,4-thiadiazol-5-yl)-thiomethyl]-ceph-3-eme-4-carboxylic acid, syn isomer of 3-acetylthiomethyl-7[(2-(2-amino-4-thiazolyl)-2-methoxyiminoacetyl}amino]-ceph-3-eme-4-carboxylic acid, syn isomer of 7-[{2-(2-amino-4-thiazolyl)-2-methoxyiminoacetyl}amino]-3-isopropyl-ceph-3-eme-4-carboxylic acid, syn isomer of 7-[{2-(2-amino-4-thiazolyl)-2-methoxyiminoacetyl}amino]-3-methyl-ceph-3-eme-4-carboxylic acid, 3-acetylthiomethyl-7-

[{2-(2-amino-4-thiazolyl)-2-methoxyiminoacetyl}-amine]-ceph-3-eme-4-carboxylic acid prepared as in Example 6, syn isomer of sodium 7-[{2-(2-amino-4-thiazolyl)-2-methoxyiminoacetyl}amino]-3-[(2-methyl-1,3,4-thiadiazol-5-yl)thiomethyl]-ceph-3-eme-4-carboxylate, syn isomer of sodium 7-[{2-(2-amino-4-thiazolyl)-2-methoxyiminoacetyl}amino]-3-[(1-methyl-tetrazol-5-yl)-thiomethyl]-ceph-3-eme-4-carboxylate, syn isomer of sodium 3-acetylthiomethyl-7-[{2-(2-amino-4-thiazolyl)-2-methoxyiminoacetyl}-amino]-ceph-3-eme-4-carboxylate and the syn isomer of crystalline sodium 3-acetylthiomethyl-7-[{2-(2-amino-4-thiazolyl)-2-methoxyiminoacetyl}amino]-ceph-3-eme-4-carboxylate.

The novel method of the invention for combatting bacterial infections in warm-blooded animals including humans comprises administering to warm-blooded animals an antibiotically effective amount of at least one compound of formula I. The compounds may be administered orally, rectally, parenterally, intramuscularly or locally by topical application to the skin or mucous. The usual effective daily dose may be 5 to 80 mg/kg depending upon the compound and the method of administration.

The novel intermediates products of the invention have the formula

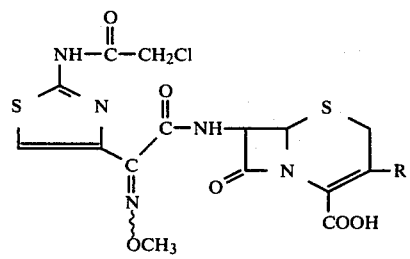

wherein R has the above definition. The said products also possess the same antibiotic properties of the compounds of formula I and may be used for the same infections.

The compounds of formula II wherein R is —CH$_2$—S—R' which are not known may be prepared by an exchange reaction beginning with 7-amino-cephalosporanic acid.

The products of formula III may be prepared by reacting thiourea with a compound of the formula

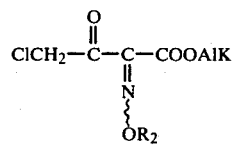

wherein R$_2$ has the above definition and AlK is alkyl of 1 to 4 carbon atoms to obtain after treatment with a base a compound of the formula

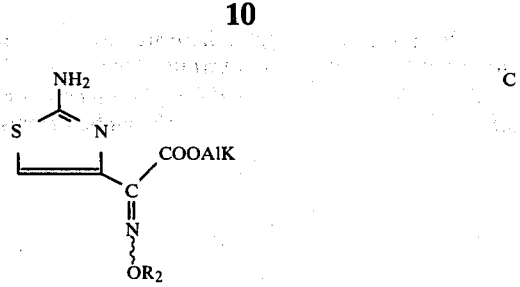

which is treated with a functional derivative of a group easily removeable by acid hydrolysis or hydrogenolysis to obtain a compound of the formula

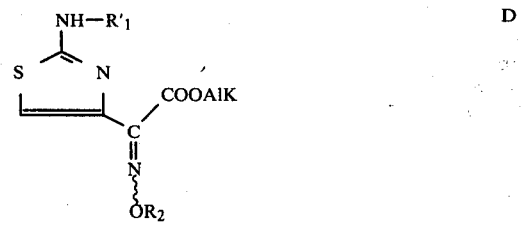

wherein R$_1'$, R$_2$ and AlK have the above definition which is treated with a base and then an acid to obtain the desired compounds of formula II.

To obtain compounds of formula III in the syn form, the reaction of thiourea and the compound of formula B is effected either in an aqueous solvent such as aqueous acetone or aqueous ethanol or at room temperature with a substantially stoichiometric amount of thiourea and for a duration of 1 to 3 hours or by a combination of the said procedures. The syn form of the products of formula C is preserved for the products of formulae D and III.

The compounds of formula B may be prepared by reaction of diazomethane or alkyl halides or sulfates with ethyl γ-chloro-α-oxyimino-acetylacetate [described in J. of Medicinal Chemistry, Vol. 16 (1973), p. 978].

The compounds of formula IV may be prepared by reacting an acid of the formula

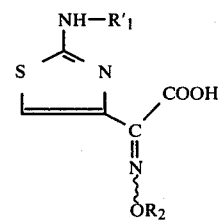

wherein R$_1'$ and R$_2$ have the above definition with 7-amino-cephalosporanic acid and optionally treating the following product with an acid hydrolysis agent or a hydrogenolysis agent. In the same fashion, the compounds of formula IV of syn configuration are obtained by reacting 7-amino-cephalosporanic acid with a compound of formula III in the syn form.

The compounds of formula III$_A$ are prepared by reacting a functional derivative of a chloroacetyl group, preferably chloroacetic acid anhydride or an chloroacetic acid halide with a compound of formula C followed by treatment with a base and an acid.

In the following examples there are described several preferred embodiments to illustrate the invention. However, it should be understood that the invention is not intended to be limited to the specific embodiments.

EXAMPLE 1

7-[{2-(2-tritylamino-4-thiazolyl)-2-methoxyimino-acetyl}amino]-3-[(2-methyl-1,3,4-thiadiazol-5-yl)-thiomethyl]-ceph-3-eme-4-carboxylic acid STEP A: ethyl γ-chloro-α-methoxyimino-acetylacetate 275 ml of a fresh solution of diazomethane (21.6 g/l) was slowly added to a mixture of 22.5 g of ethyl γ-chloro-α-oximino-acetylacetate in 100 ml of methylene chloride in an ice bath and after standing for 5 minutes, excess diazomethane was destroyed with a little alumina. The mixture was concentrated to dryness and the residue was chromatographed over silica gel. Elution with methylene chloride yielded 11.93 g of ethyl γ-chloro-α-methoxyimino-acetylacetate.

STEP B: ethyl 2-(2-amino-4-thiazolyl)-2-methoxyimino-acetate

A mixture of 1 g of the product of Step A, 3 ml of absolute ethanol and 0.42 g of ground thiourea was stirred for 2 hours at room temperature and was diluted with 60 ml of ether. The mixture was stirred and was vacuum filtered. The recovered product was washed and dried to obtain 685 mg of hydrochloride. The latter was dissolved in 4 ml of water at 50° C. and potassium acetate was added to adjust the pH to 6. The mixture was vacuum filtered and the product was washed with water and dried to obtain 270 mg of ethyl 2-(2-amino-4-thiazolyl)-2-methoxyimino-acetate melting at 161° C. having the syn configuration. RMN (CDCl$_3$ 60 MHz) ppm: 4.0 (N-OCH$_3$), 6.7 (proton of thiazole ring)

STEP C: ethyl 2-(2-tritylamino-4-thiazolyl)-2-methoxyiminoacetate 2.9 ml of triethylamine were added at −10° C. to a mixture of 4.6 g of the product of Step A dissolved at 30° C. in 92 ml of methylene chloride and the mixture was cooled to −35° C. 6.1 g of trityl chloride were added thereto over 15 minutes and after returning the temperature to room temperature, the mixture stood for 2½ hours. The mixture was washed with water, then 0.5 N hydrochloric acid and aqueous sodium acetate and was dried. The mixture was concentrated to dryness and the residue was taken in ether. The solution was concentrated to dryness and the mixture was dissolved in methanol. Water and ether were added thereto and the mixture was allowed to crystallize. The mixture was vacuum filtered and the product was washed with ether to obtain 6.15 g of ethyl 2-(2-tritylamino-4-thiazolyl)-2-methoxyimino-acetate melting at 120° C. with a syn configuration.

STEP D: sodium 2-(2-tritylamino-4-thiazolyl)-2-methoxyiminoacetate

A mixture of 7.01 g of the product of Step C in 35 ml of dioxane was heated to 110° C. on an oil bath and 9 ml of 2 N sodium hydroxide were added over 5 minutes. The mixture was refluxed with stirring for 30 minutes and the mixture was cooled and vacuum filtered. The precipitate was washed with dioxane and then ether to obtain a first crop of 5.767 g of product and the filtrate was concentrated to obtain a second crop of 1.017 g for a total yield of 6.784 g of sodium 2-(2-tritylamino-4-thiazolyl)-2-methoxyimino-acetate with a syn configuration.

STEP E: 7-[{2-(2-tritylamino-4-thiazolyl)-2-methoxyiminoacetyl}amino]-3-[(2-methyl-1,3,4-thiadiazol-5-yl)-thiomethyl]ceph-3-eme-4-carboxylic acid A mixture of 2.5 g of the product of Step D, 40 ml of methylene chloride and 5 ml of 2 N hydrochloric acid was decanted and the organic phase was washed with water, dried and evaporated. The raw product was dissolved in 30 ml of dry tetrahydrofuran and after the addition of 0.7 g of dicyclohexylcarbodiimide, the mixture was stirred at room temperature for 45 minutes and was vacuum filtered. The filtrate was cooled to −5° C. and a solution of 0.895 g of 7-amino-3-[(2-methyl-1,3,4-thiadiazol-5-yl)-thiomethyl]-ceph-3-eme-4-carboxylic acid in 10 ml of water and 0.9 ml of triethylamine precooled to 0° was added thereto. The mixture stood for 90 minutes at room temperature and the tetrahydrofuran was evaporated. 40 ml of methylene chloride were added and the mixture was washed with dilute hydrochloric acid and then water, was dried and evaporated to dryness. The residue was dissolved in 8 ml of dioxane and 3 ml of saturated sodium bicarbonate solution were added dropwise. The mixture was stirred for 30 minutes and was filtered. The solid product was washed with ether to obtain 0.554 g of the starting acid in the form of its sodium salt. The dioxane was evaporated from the filtrate and the residue was taken up in methylene chloride. The solution was washed with N hydrochloric acid, then with water, was dried and was evaporated to dryness. The residue was triturated with ether, was vacuum filtered and washed to obtain 1.9 g of raw product. The product in 5 ml of ethyl acetate was stirred and 5 ml of ether were added with stirring. The mixture was vacuum filtered and the product was washed to obtain 1.47 g of partially purified product. The latter was dissolved in 2 ml of methylene chloride and 25 ml of ether were added. The mixture was vacuum filtered and the product was washed to obtain 1.4 g of 7-[{2-(2-tritylamino-4-thiazolyl)-2-methoxyiminoacetyl}amino]-3-[(2-methyl-1,3,4-thiadiazol-5-yl)-thiomethyl]-ceph-3-eme-4carboxylic acid in the syn form.

EXAMPLE 2

7-[{2-(2-amino-4-thiazolyl)-2-methoxyiminoacetyl}-amino]-3-[(2-methyl-1,3,4-thiadiazol-5-yl)-thiomethyl]-ceph-3-eme-4-carboxylic acid A mixture of 1.4 g of the product of Example 1 and 5 ml of 50% aqueous formic acid was heated at 57° C. for 15 minutes and 5 ml of water were added. The mixture was cooled to room temperature and was vacuum filtered. The product was washed with ethanol and ether to obtain 0.687 g of raw product which was dissolved in 7 ml of water and 0.2 ml of triethylamine. The mixture was vacuum filtered and the filter was rinsed. The filtrate was acidified with 0.2 ml of 50% aqueous formic acid and the mixture was stirred and vacuum filtered. The product was washed with alcohol and ether to obtain 0.275 g of 7-[{2-(2-amino-4-thiazolyl)-2-methoxyiminoacetyl}amino]-3-[(2-methyl-1,3,4-thiadiazol-5-yl)-thiomethyl]-ceph-3-eme-4-carboxylic acid with a syn configuration.

Analysis: $C_{17}H_{17}O_5N_7S_4$ (0.5 EtOH) Calculated: %C, 39.25; %H, 3.66; %N, 17.80; %S, 23.28. Found: %C, 39.3; %H, 3.5; %N, 17.9; %S, 23.1.

RMN (DMSO, 60 MHz) ppm: 3.85 (N—OCH₃), 6.76 (proton of thiazol ring).

EXAMPLE 3

7-[{2-(2-tritylamino-4-thiazolyl)-2-methoxyiminoacetyl}amino]-3-[(1-methyl-tetrazol-5-yl)-thiomethyl]-cephem-3-eme-4-carboxylic acid 2.33 g of the sodium salt of 2-(2-tritylamino-4-thiazolyl)-2-methoxyimino-acetic acid were reacted as in Example 1 to obtain a raw acid which was dissolved in 30 ml of methylene chloride. 0.7 g of dicyclohexylcarbodiimide were added to the mixture which was then stirred under an inert gas at room temperature for 50 minutes. The mixture was filtered and the filtrate was cooled to −5° C. A solution of 0.854 g of 7-amino-3-[(1-methyltetrazol-5-yl)-thiomethyl]-ceph-3-eme-4-carboxylic acid in 10 ml of methylene chloride and 0.75 ml of triethylamine was added all at once thereto and after returning the temperature to room temperature, 1 ml of acetic acid was added. After 10 minutes, the mixture was vacuum filtered and the filtrate was washed with aqueous hydrochloric acid, dried and evaporated to dryness. The residue was taken up in 8 ml of dioxane and 2.5 ml of an aqueous solution saturated with sodium bicarbonate were added thereto. The mixture was vacuum filtered and the product was rinsed with a 1-1 ether-dioxane mixture and then with ether. The filtrate was evaporated to dryness and the residue was taken up in methylene chloride. The solution was washed with aqueous hydrochloric acid, was dried and evaporated to dryness. The residue was triturated with ether and was vacuum filtered. The product was washed with ether to obtain 2.29 g of raw product. The product in ethanol was stirred at 10° C. for an hour and was vacuum filtered. The product was washed with ether to obtain 1.42 g of purified 7-[{2-(2-tritylamino-4-thiazolyl)-2-methoxyiminoacetyl}amino]-3-[(1-methyl-tetrazol-5-yl)-thiomethyl]-ceph-3-eme-4-carboxylic acid in the syn configuration.

EXAMPLE 4

7-[{2-(2-amino-4-thiazolyl)-2-methoxyiminoacetyl}-amino]-3-[(1-methyl-tetrazol-5-yl)-thiomethyl]-ceph-3-eme-4-carboxylic acid A mixture of 1.4 g of the product of Example 3 and 5 ml of 50% aqueous formic acid was held on a water bath at 55° C. for 15 minutes and then 5 ml of water were added. The mixture was cooled and vacuum filtered and the filtrate was concentrated after the addition of 5 ml of ethanol. The residue was taken up in 5 ml of ethanol and the mixture was triturated and was vacuum filtered. The product was washed with ethanol and then ether, was vacuum filtered, dried and washed to obtain 0.557 g of pure 7-[{2-amino-4-thiazolyl)-2-methoxyiminoacetyl}amino]-3-[(1-methyl-tetrazol-5-yl)-thiomethyl]-ceph-3-eme-4-carboxylic acid in the syn configuration.

Analysis: $C_{16}H_{17}O_5N_9S_3$ (0.5 EtOH) Calculated: %C, 38.19; %H, 3.77; %N, 23.58; %S, 18.00. Found: %C, 38.1; %H, 3.9; %N, 22.5; %S, 17.7.

RMN (DMSO 60 MHz): ppm: 3.83 (NOCH₃) and 6.73 (proton of thiazole ring).

EXAMPLE 5

3-acetylthiomethyl 7-[{2-(2-tritylamino-4-thiazolyl)-2-methoxyimino}acetylamino]-ceph-3-eme-4-carboxylic acid

STEP A:
7-amino-3-acetylthiomethyl-ceph-3-eme-4-carboxylic acid 1.7 g of sodium bicarbonate were added under an inert gas to a stirred mixture of 5.44 g of 7-amino-cephalosporanic acid in 50 ml of water containing 1% of hydroquinone and after dissolution occured, 3 g of potassium thioacetate were added thereto. The mixture was stirred for 3 hours at 60° C. and was then cooled and acidified with acetic acid. The mixture was stirred at room temperature and was vacuum filtered and the product was washed and dried to obtain 4.9 g of 7-amino-3-acetylthiomethyl-ceph-3-eme-4-carboxylic acid.

STEP B:
3-acetylthiomethyl-7-[{2-(2-tritylamino-4-thiazolyl)-2-methoxyimino}acetylamino]-ceph-3-eme-4-carboxylic acid 3.1 g of sodium 2-[(2-tritylamino-4-thiazolyl)-2-methoxyimino]-acetate in 40 ml of methylene chloride and 6.5 ml of 2 N hydrochloric acid were reacted to form the free acid which was then dissolved in 30 ml of methylene chloride. 0.8 g of dicyclohexylcarbodiimide were added to the mixture which was then stirred for 90 minutes in an ice-water bath. The mixture was vacuum filtered and the filtrate was cooled to −5° C. A solution of 1.1 g of 7-amino-3-acetylthiomethyl-ceph-3-eme-4-carboxylic acid in 13 ml of methylene chloride and 0.9 ml of triethylamine cooled to 0° C. was added to the filtrate and the temperature of the mixture was allowed to return to room temperature. 1 ml of acetic acid was added thereto and the mixture was vacuum filtered. The filtrate was washed with water containing hydrochloric acid, then with water and was evaporated to dryness. The residue was taken up in dioxane and 3.5 ml of an aqueous solution saturated with sodium bicarbonate were added thereto. The mixture was vacuum filtered after 30 minutes and the recovered product was washed with a dioxane-ether mixture to obtain 0.64 g of the sodium salt of the starting trityl acid. The filtrate was evaporated to dryness and the residue was taken up in 30 ml of methylene chloride. The solution was washed with water containing hydrochloric acid (10 ml of water plus 10 ml of 2 N hydrochloric acid) and then with water and evaporated to dryness. The residue was triturated with 25 ml of ether, was vacuum filtered and dried to obtain 1.89 g of raw product. The latter was crystallized twice from 3 ml of ethyl acetate by addition of 25 ml of ether to obtain 0.89 g of 3-acetylthiomethyl-7-[{2-(2-tritylamino-4-thiazolyl)-2-methoxyimino}acetylamino]-ceph-3-eme-4-carboxylic acid in the syn configuration.

EXAMPLE 6

3-acetylthiomethyl-7-[{2-(2-amino-4-thiazolyl)-2-methoxyimino)acetylamino]-ceph-3-eme-4-carboxylic acid The product of Example 5 and 5 ml of 50% aqueous formic acid were stirred in a bath at 55° C. for 15 minutes and then 5 ml of water were added. The mixture was cooled to room temperature and was vaccum filtered. 5 ml of ethanol were added to the filtrate and the mixture was evaporated to dryness. The residue effloresced in 5 ml of alcohol to obtain in 2 crops 440 mg of raw product. The latter was dissolved in 6 ml of 50% aqueous acetone and 20 mg of carbon black were added thereto. The mixture was vacuum filtered and the acetone was partially evaporated from the filtrate which was then vacuum filtered to obtain 0.265 g of pure 3-acetylthiomethyl-7-[{2-(2-amino-4-thiazolyl)-2-methoxyimino}acetylamino]-3-ceph-4-eme-carboxylic acid in the syn configuration.

Analysis: $C_{16}H_{17}O_6N_5S_3$ (0.25 $CH_3COCH_3$) Calculated: %C, 41.39; %H, 3.83; %N, 14.41; %S, 19.78. Found: %C, 41.2; %H, 3.8; %N, 14.4; %S, 19.8.

RMN Spectrum (DMSO 60 MHz): ppm: 3.83 ($NOCH_3$) and 6.73 (proton of thiazole ring).

EXAMPLE 7 tert.-butyl 7-[{2-(2-tritylamino-4-thiazolyl)-2-methoxyimino}acetylamino]-3-isopropyl-ceph-3-eme-4-carboxylate 1.65 g of sodium [(2-tritylamino-4-thiazolyl)-2-methoxyimino]-acetate was reacted as in Example 1 to obtain the free acid which was then dissolved in 25 ml of methylene chloride. 0.71 g of dicyclohexylcarbodiimide were added to the solution and after stirring the mixture for 10 minutes in an ice-water bath, 0.965 g of tert.-butyl 7-amino-3-isopropyl-ceph-3-eme-4-carboxylate were added thereto. The mixture was stirred for 2 hours at room temperature and was then vacuum filtered. The filtrate was washed with 10 ml of water containing 2 ml of 2 N hydrochloric acid, then with water and finally with a mixture of 10 ml of water and 5 ml of a saturated sodium bicarbonate solution, was dried and evaporated to dryness. The residue was dissolved in ether and the mixture was vacuum filtered. The solid product was washed with isopropyl ether to obtain 1.66 g of tert.-butyl 7-[{2-(2-tritylamino-4-thiazolyl)-2-methoxyimino}acetylamino]-3-isopropyl-ceph-3-eme-4-carboxylate in the syn configuration.

EXAMPLE 8

7-[{2-(2-amino-4-thiazolyl)-2-methoxyimino}acetylamino]-3-isopropyl-ceph-3-eme-4-carboxylic acid A mixture of 1.66 g of the product of Example 7 and 6 ml of trifluoroacetic acid was stirred at room temperature for 15 minutes and after 60 ml of isopropyl ether were added thereto, the mixture was vacuum filtered. The solid product was washed with isopropyl ether to obtain 0.825 g of product in the form of a salt of trifluoroacetic acid. The product was dissolved in 6 ml of water and 4 ml of acetone and 0.2 ml of pyridine was added to the solution. The acetone was evaporated to obtain a first crop of 0.232 g of product and the filtrate was evaporated to dryness. The residue was dissolved in 3 ml of water to isolate 0.194 g of additional product for a total yield of 0.426 g of 7-[{2-(2-amino-4-thiazolyl)-2-methoxyimino}acetylamino]-3-isopropyl-ceph-3-eme-4-carboxylic acid in the syn configuration.

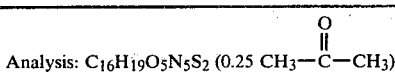

Analysis: $C_{16}H_{19}O_5N_5S_2$ (0.25 $CH_3-\overset{O}{\underset{\|}{C}}-CH_3$)

| | % C | % H | % N | % S |
|---|---|---|---|---|
| Calculated: | 46.23 | 4.88 | 15.41 | 14.10 |
| Found: | 46.1 | 4.7 | 15.5 | 14.1 |

RMN Spectrum (DMSO 60 MHz) ppm: 3.83 ($NOCH_3$) and 6.78 (proton of thiazole ring).

EXAMPLE 9 tert.-butyl 7-[{2-(2-tritylamino-4-thiazolyl)-2-methoxyimino}acetylamino]-3-methyl-ceph-3-eme-4-carboxylic acid 2.3 g of sodium 2-[(2-tritylamino-4-thiazolyl)-2-methoxyimino]acetate were reacted as in Example 1 to form the free acid which was dissolved in 30 ml of methylene chloride and 1.1 g of dicyclohexylcarbodiimide were added to the solution. After 5 minutes, 1.35 g of tert.-butyl 7-amino-desactoxy-cephalosporanate were added to the mixture and the mixture was stirred for 2 hours and was vacuum filtered. The filtrate was washed with water, water acidified with hydrochloric acid, then with water and finally with a solution saturated with sodium bicarbonate. The solution was dried and evaporated to dryness. The residue was taken up in ether and the solution was vacuum filtered. The filtrate was evaporated to dryness to obtain 2.8 g of pure tert.-butyl 7-[{2-(2-tritylamino-4-thiazolyl)-2-methoxyimino}acetylamino]-3-methyl-ceph-3-eme-4-carboxylate in the syn configuration.

EXAMPLE 10

7-[{2-(2-amino-4-thiazolyl)-2-methoxyimino}acetylamino]-3-methyl-ceph-3-eme-4-carboxylic acid A mixture of 2.3 g of the product of Example 9 and 8 ml of trifluoroacetic acid was stirred for 15 minutes at room temperature and 80 ml of isopropyl ether were added thereto. The mixture was stirred and vacuum filtered and the product was washed with isopropyl ether to obtain 1.12 g of a product in the form of a trifluoroacetic acid salt. The latter was dissolved in 10 ml of ethanol at 40° C. and crystallization was induced by addition of 0.2 ml of pyridine. The mixture was cooled to 10° C. and was vacuum filtered. The product was washed with ethanol and ether to obtain 0.531 g of pure 7-[2-(2-amino-4-thiazolyl)-2-methoxyimino acetylamino]-3-methyl-ceph-3-eme-4-carboxylic acid in the syn configuration.

Analysis: $C_{14}H_{15}O_5N_5S_2$ (0.25 EtOH). Calculated: %C, 42.6; %H, 4.06; %N, 17.13; %S, 15.68. Found: %C, 42.2; %H, 3.9; %N, 16.6; %S, 15.5.

RMN Spectrum (DMSO 60 MHz) ppm: 3.85 ($NOCH_3$) and 6.78 (proton of thiazole ring).

EXAMPLE 11

7-[{2-(2-tritylamino-4-thiazolyl)-2-methoxyiminoacetyl}amino]-3-[(1-methyl-tetrazol-5-yl)-thiomethyl]-ceph-3-eme-4-carboxylic acid A mixture of 2.7 g of 3-acetoxymethyl-7-[{2-(2-tritylamino-4-thiazolyl}amino]-ceph-3-eme-4-carboxylic acid, 0.624 g of monosodium phosphate, 1.51 g of sodium bicarbonate, 1.32 g of 1-methyl-5-mercapto-thiazole, 40 ml of water and 20 ml of acetone stood overnight at 48° C. and then one hour at 60° C. After purification, the product in the syn configuration obtained was identical to that of Example 3.

EXAMPLE 12

7-[{2-(2-amino-4-thiazolyl)-2-methoxyiminoacetyl}-amino]-3-[(1-methyl-tetrazol-5-yl)-thiomethyl]-ceph-3-eme-4-carboxylic acid

STEP A:
3-acetoxymethyl-7-[{2-(2-tritylamino-4-thiazolyl)-2-methoxylaminoacetyl}amino]-ceph-3-eme-4-carboxylic acid A mixture of 3.06 g of sodium 2-(2-tritylamino-4-thiazolyl)-2-methoxyimino acetate, 65 ml of methylene chloride and 6.5 ml of 2 N hydrochloric acid was washed with water, dried and concentrated to dryness to obtain a quantitative yield of the free acid. The latter was dissolved in 30 ml of dry methylene chloride and 0.78 g of dicyclohexylcarbodiimide were added thereto. The mixture was stirred for one hour at room temperature and was vacuum filtered. The filtrate was cooled to −10° C. and a solution of 1.01 g of 7-amino-cephalosporanic acid in 13 ml of methylene chloride and 0.9 ml of triethylamine was added thereto. The temperature was returned to room temperature and then 1 ml of acetic acid was added thereto. The mixture was vacuum filtered and the filtrate was washed with water containing hydrochloric acid, with water, dried and evaporated to dryness. The residue was taken up in 10 ml of dioxane and 1 ml of water and 3 ml of water saturated with sodium bicarbonate were added thereto. The mixture was stirred and vacuum filtered and the filtrate was washed and concentrated to dryness. The residue was taken up in methylene chloride and the solution was washed with a mixture of 10 ml of water and 5 ml of N hydrochloric acid. The mixture was decanted and the organic phase was washed with water and evaporated to dryness. The residue effloresced in ether to obtain 1.747 g of raw product which was dissolved in ethyl acetate followed by precipitation with ether to obtain 1.255 g of pure 3-acetoxymethyl-7-[{2-(2-tritylamino-4-thiazolyl)-2-methoxyiminoacetyl}amino]-ceph-3-eme-4-carboxylic acid in the syn configuration.

STEP B:
3-acetoxymethyl-7-[{2-(2-amino-4-thiazolyl)-2-methoxyiminoacetyl}amino]-ceph-3-eme-4-carboxylic acid A mixture of 0.975 g of the product of Step A and 4 ml of 50% aqueous formic acid was stirred for 10 minutes at 55° C. and after the addition of 4 ml of water, the mixture was vacuum filtered. The filtrate was evaporated under reduced pressure to dryness and the residue was effloresced with 2 ml of ethanol. The mixture was vacuum filtered and the product was washed with ethanol and then ether to obtain 0.428 g of pure 3-acetoxymethyl-7-[{2-(2-amino-4-thiazolyl)-2-methoxyiminoacetyl}amino]-ceph-3-eme-4-carboxylic acid in the syn configuration.

RMN Spectrum (DMSO 60 MHz) ppm: 2.03

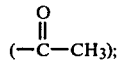

doublet 9.58, J=8 Hz (—CONH); 6.76 (proton of thiazole ring)

STEP C:
7-[{2-(2-amino-4-thiazolyl)-2-methoxyiminoacetyl}-amino]-3-[(1-methyltetrazol-5-yl)-thiomethyl]-ceph-3-eme-4-carboxylic acid A mixture of 1.7 g of the product of Step B, 0.624 g of monosodium phosphate, 1.51 g of sodium bicarbonate, 1.32 g of 1-methyl-5-mercapto-thiazole, 40 ml of water and 20 ml of acetone was held overnight at 48° C. and for one hour at 60° C. to obtain a product in the syn configuration identical to that of Example 1.

EXAMPLE 13

7-[{2-(2-tritylamino-4-thiazolyl)-2-methoxyiminoacetyl}amino]-3-methyl-ceph-3-eme-4-carboxylic acid

STEP A: anti isomer of ethyl 2-[2-amino-4-thiazolyl]-2-(methoxyimino)-acetate 330 ml of 2 N sodium hydroxide were added over an hour to a cooled mixture of 116 g of ethyl 4-chloro-2-oximinoacetoacetate, 360 ml of anhydrous acetone and 66 ml of methyl sulfate and after stirring for 105 minutes, 45.6 g of thiourea were added thereto. The mixture was heated to 53° C. for 25 minutes and the acetone was distilled. The residue was taken up in 180 ml of isopropyl ether and after stirring the mixture 41.3 g of potassium carbonate were added thereto. The mixture was filtered to recover 21.1 g of syn product and the filtrate was decanted. The aqueous phase was extracted with 100 ml of isopropyl ether and the organic phase was dried and vacuum filtered. 13 ml of 10 N ethanoic hydrochloric acid were added to the filtrate and the hydrochloride salt crystallized. The mixture was vacuum filtered and the product was rinsed with isopropyl ether and dried to obtain 32 g of the hydrochloride salt of anti product.

55.85 g of the said hydrochloride salt were dissolved in 275 ml of methanol containing 20% water and the mixture was heated to reflux and was cooled for crystallization. The mixture was diluted with 550 ml of ether, stirred for half hour, rinsed with a 2-1 methanol-ether mixture and evaporated to dryness to obtain 34.85 g of pure hydrochloride of anti product. A mixture of 29.3 g of the said hydrochloride, 110 ml of water, 110 ml of methylene chloride and 110 ml of an aqueous 10% sodium bicarbonate solution was stirred and decanted. The aqueous phase was extracted with methylene chloride and the organic extracts were dried and evaporated to dryness. The residue was taken up in ether and the mixture was stirred and vacuum filtered. The product was rinsed with ether and dried to obtain 20.4 g of the anti isomer of ethyl 2-(2-amino-4-thiazolyl)-2-(methoxyimino)-acetate melting at 115° C.

RMN Spectrum (CDCl₃ 60 MHz) ppm: 4.08 (NOCH₃); 7.5 (proton of thiazole ring).

STEP B: anti isomer of ethyl 2-(2-tritylamino-4-thiazolyl)-2-methoxyimino-acetate 15.1 g of trityl chloride were added over 20 minutes to a cooled mixture of 11.45 g of the product of Step A, 23 ml of dry dimethylformamide, 45 ml of dry methylene chloride and 7 ml of triethylamine and 50 ml of hydrochloric acid were added thereto with stirring. The mixture was decanted and the aqueous phase was extracted with methylene chloride. The organic extracts were washed with water, reextracted, dried and vacuum filtered. The filtrate was evaporated to dryness to obtain 30.1 g of raw anti isomer of ethyl 2-(2-tritylamino-4-thiazolyl)-2-methoxyimino-acetate.

STEP C: anti isomer of 2-(2-tritylamino-4-thiazolyl)-2-methoxyimino-acetic acid 25 ml of 2 N sodium hydroxide were added to a stirred mixture of 30.1 g of the product of Step B, 150 ml of dioxane, 5 ml of sodium hydroxide in a water bath and after stirring for an hour, crystallization of the sodium salt formed was effected over 15 minutes. The mixture was vacuum filtered and the product was washed with a 1-1 dioxane-ether mixture and then with ether and dried to obtain 18.4 g of the sodium salt. The latter was added to a mixture of 250 ml of methylene chloride, 100 ml of water and 50 ml of N hydrochloric acid and the mixture was stirred for 10 minutes and was decanted. The aqueous phase was extracted with methylene chloride and the organic extracts were washed twice with water, reextracted, dried and vacuum filtered. The filtrate was evaporated to dryness and the residue was taken up in ether. The product effloresced and was vacuum filtered. The product was rinsed with ether and dried to obtain 13.85 g of the anti isomer of 2-(2-tritylamino-4-thiazolyl)-2-methoxyimino-acetic acid melting at 220° C.

RMN Spectrum (CDCl$_3$ 60 MHz) ppm: 4.2 (OCH$_3$) and 7.32 (proton of thiazole ring).

EXAMPLE 14 anti isomer of diethylamine salt of 7-[{2-(2-tritylamino-4-thiazolyl)-2-methoxyiminoacetyl}amino]-3-methyl-ceph-3-eme-4-carboxylic acid The acid of Example 13 was dissolved in about 7 ml of dioxane under argon with stirring and then 0.65 ml of diethylamine were added thereto at room temperature. Crystallization slowly started and the mixture was stirred at room temperature for 20 minutes and was then vacuum filtered. The solid was washed twice with 2 ml of dioxane and the solution was diluted with dioxane. 110 ml of isopropyl ether were added thereto to cause crystallization and the mixture was slowly stirred for an hour. The mixture was filtered and the product was washed with isopropyl ether and was dried to obtain 1.94 g of practically pure anti isomer of the diethylamine salt of 7-[{2-(2-tritylamino-4-thiazolyl)-2-methoxyiminoacetyl}amino]-3-methyl-ceph-3-eme-4-carboxylic acid.

EXAMPLE 15 anti isomer of 7-[{2-(2-amino-4-thiazolyl)-2-methoxyiminoacetyl}-amino]-3-methyl-ceph-3-eme-4-carboxylic acid The salt of Example 14 was dissolved in 50 ml of methylene chloride and the solution was washed twice with 25 ml of N hydrochloric acid and once with 25 ml of water. The aqueous phases were extracted with methylene chloride and the combined organic extracts were dried and concentrated to dryness under reduced pressure to obtain 1.72 g of the anti isomer of 7-[{2-(2-tritylamino-4-thiazolyl)-2-methoxyiminoacetyl}amino]-3-methyl-ceph-3-eme-4-carboxylic acid. The said product was added under argon to 8.6 ml of 50% aqueous formic acid and the mixture was stirred for 20 minutes in an oil bath at 60° C. The mixture was vacuum filtered and the filtrate was washed with aqueous formic acid and then with water. 10 ml of ethanol were added to the aqueous phase and the mixture was concentrated under reduced pressure without heating above 35° C. and without arriving at dryness. The mixture was then taken up in 5 ml of a 1-1 ethanol-water mixture and crystallization was effected. The mixture was concentrated to dryness and the residue was taken up in ethanol. The mixture was stirred and vacuum filtered and the solid product was washed with ethanol, then with ether and dried to obtain 400 mg of the anti isomer of 7-[{2-(2-amino-4-thiazolyl)-2-methoxyiminoacetyl}-amino]-3-methyl-ceph-3-eme-4-carboxylic acid.

Analysis: C$_{14}$H$_{15}$O$_5$N$_5$S$_2$ (0.5 H$_2$O). Calculated: %C, 41.1; %H, 3.9; %N, 17.2; %S, 15.7. Found: %C, 40.9; %H, 3.9; %N, 17.5; %S, 15.7.

RMN Spectrum (DMSO 60 MHz) ppm: 3.96 (NOCH$_3$) and 7.48 (proton of thiazole ring).

EXAMPLE 16 anti isomer of 3-acetylthiomethyl-7-[{2-(2-tritylamino-4-thiazolyl)-2-methoxyiminoacetyl}amino]-ceph-3-eme-4-carboxylic acid A mixture of 2.22 g of the anti isomer of 2-(2-tritylamino-4-thiazolyl)-2-methoxyimino-acetic acid, 20 ml of dry tetrahydrofuran, 15 ml of methylene chloride and 0.55 ml of N-methyl-morpholine under argon was cooled to −20° C. and 0.65 ml of isobutyl chloroformate was added thereto. The mixture was stirred and was cooled to −35° C. and then a solution of 1.44 g of 7-amino-3-acetylthiomethyl-ceph-3-eme-4-carboxylic acid, 25 ml of methylene chloride and 1.4 ml of anhydrous triethylamine was added thereto. The mixture spontaneously heated up and the solvents were removed. The residue was taken up in methylene chloride and 7 ml of N hydrochloric acid and the mixture was vacuum filtered. The filtrate was decanted and the aqueous phase was extracted with methylene chloride. The organic phase was washed with water, dried and vacuum filtered. The filtrate was evaporated to dryness to obtain 4.58 g of raw anti isomer of 3-acetylthiomethyl-7-[{2-(2-tritylamino-4-thiazolyl)-2-methoxyiminoacetyl}amino]-ceph-3-eme-4-carboxylic acid.

EXAMPLE 17 anti isomer of 3-acetylthiomethyl-7-[{2-(2-amino-4-thiazolyl)-2-methoxyiminoacetyl}amino]-ceph-3-eme-4-carboxylic acid A mixture of 4.58 g of the product of Example 16 and 30 ml of 50% aqueous formic acid was heated at 55° C. for 20 minutes and crystallization occured. The mixture was cooled and was diluted and stirred. The mixture was vacuum filtered and the product was rinsed and dried to obtain 1.257 g of triphenyl carbinol. The filtrate was evaporated to dryness under reduced pressure and the residue was taken up in water. Crystallization occured and the mixture was stirred for 30 minutes and was vacuum filtered. The solid was rinsed and dried to obtain 1.68 g of raw product. The latter was dissolved in 4 ml of a molar solution of sodium bicarbonate and the insolubles were ground up. The mixture was vacuum filtered and the filtrate was rinsed with water. 0.24 ml of acetic acid were added to the filtrate and the mixture was vacuum filtered. The precipitate was rinsed with water and dried to obtain 426 mg of purified product. 0.15 ml of formic acid were added to the filtrate and crystallization occured. The mixture was vacuum filtered and the product was rinsed with water and dried to obtain 505 mg of more pure anti isomer of 3-acetylthiomethyl-7-[{2-(2-amino-4-thiazolyl)-2-methoxyiminoacetyl}amino]-ceph-3-eme-4-carboxylic acid melting at 190° C.

Analysis: $C_{16}H_{17}O_6N_5S_3$. Calculated: %C, 40.76; %N, 14.85; %S, 20.40. Found: %C, 41.3; %N, 14.4; %S, 19.2.

RMN Spectrum (DMSO 60 MHz) ppm: 3.95 ($NOCH_3$) and 7.45 (proton of thiazole ring).

| U.V. Spectrum (EtOH, N/10 HCl): | | |
| --- | --- | --- |
| max. at 239 nm | $E' = 383$ | $\epsilon = 18,000$ |
| max. at 254 nm | $E' = 384$ | $\epsilon = 18,100$ |
| Inflex. towards 280 nm | $E' = 249$ | |

EXAMPLE 18 syn isomer of 3-acetylthiomethyl-7-[{2-(2-amino-4-thiazolyl)-2-methoxyiminoacetyl}amino]-ceph-3-eme-4-carboxylic acid A solution of the syn isomer of 4.55 g of 3-acetoxymethyl-7-[{2-(2-amino-4-thiazolyl)-2-methoxyiminoacetyl}amino]-ceph-3-eme-4-carboxylic acid, 1.7 g of potassium thioacetate. 2 g of deshydrated monosodium phosphate 1.05 g sodium acid carbonate and 20 ml of distilled water was heated at 70° C. for 90 minutes and the mixture was acidified with 2 ml of formic acid and was extracted 4 times with 60 ml of methyl acetate (insolubles vacuum filtered). The organic solution was washed with water and evaporated to dryness. The residue was dissolved in 20 ml of acetone containing 10% of water and 0.5 g of activated carbon were added thereto. The mixture was stirred for 5 minutes and was vacuum filtered and the filter was washed with acetone containing 10% of water. The filter eas evaporated to dryness and the residue was treated with absolute ethanol and was vacuum filtered. The product was washed with alcohol and then with ether to obtain 1.9 g of the pure syn isomer of 3-acetylthiomethyl-7-[{2-(2-amino-4-thiazolyl)-2-methoxyiminoacetyl}amino]-ceph-3-eme-4-carboxylic acid which was identical to the product of Example 6.

RMN Spectrum (DMSO 60 MHz) ppm: 3.85 ($NOCH_3$) and 6.75 (proton of thiazole ring).

EXAMPLE 19 syn isomer of sodium 7-[{2-(2-amino-4-thiazolyl)-2-methoxyiminoacetyl}-amino]-3-[(2-methyl-1,3,4-thiadiazol-5-yl)-thiomethyl]-ceph-3-eme-4-carboxylate An aqueous solution of sodium bicarbonate was added to a solution of 2.3 g of the syn isomer of Example 2 in 5 ml of acetone to maintain a pH of 7 and 0.4 g of animal black was added. The mixture was stirred for 5 minutes and vacuum filtered. The filtrate was washed with a 1-1 acetone-water mixture and 50 ml of ethanol were added to the decolorized filtrate. The mixture was evaporated to dryness under reduced pressure at 30° C. and the residue was taken up in 5 ml of ethanol. The crystals were triturated and vacuum filtered. The product was washed with ethanol and then ether to obtain 1.3 g of the syn isomer of sodium 7-[{2-(2-aminothiazolyl)-2-methoxyiminoacetyl}amino]-3-[(2-methyl-1,3,4-thiadiazol-5-yl)-thiomethyl]-ceph-3-eme-4-carboxylate. Sodium analysis: calculated 4.18%, Found 4.70%.

| Ultra violet spectrum (ethanol): | | |
| --- | --- | --- |
| max. at 235 nm | $E' = 360$ | $\epsilon = 19,800$ |
| 265 nm | $E' = 322$ | $\epsilon = 17,700$ |
| Inflex towards 280 nm | $E' = 295$ | |
| (ethanol-N/10 hydrochloric acid): | | |
| Inflex. towards 218 nm | $E' = 244$ | |
| max. at 266–267 nm | $E' = 406$ | $\epsilon = 22,300$ |
| Inflex. towards 280 nm | $E' = 363$ | |

EXAMPLE 20 syn isomer of sodium 7-[{2-(2-amino-4-thiazolyl)-2-methoxyiminoacetyl}-amino]-3-[(1-methyl-tetrazol-5-yl)-thiomethyl]-ceph-3-eme-4-carboxylate A mixture of 3.35 g of the syn isomer of Example 4, 7 ml of methanol and 7 ml of a molar solution of aqueous sodium bicarbonate solution was stirred for 5 minutes at room temperature and was vacuum filtered. The filter was rinsed twice with a 1-1 water-methanol mixture and 85 ml of ethanol were added to the filtrate to crystallize the sodium salt. Then, 170 ml of ether were added thereto and the mixture was stirred for 10 minutes and was vacuum filtered. The solid product was washed with a 1-1 ether-ethanol mixture, then ether and dried to obtain 3.26 g of product. The latter was dissolved in 40 ml of water and 0.6 ml of acetic acid were added to the solution to obtain a pH of 6.8–7. The mixture was diluted with ethanol and the solvents were evaporated under reduced pressure at a temperature less than 35° C. The residue was taken up in ethanol to remove water and was evaporated to dryness. The residue was taken up in 16 ml of methanol which was then diluted with 160 ml of acetone to crystallize the product. The mixture was stirred for 5 minutes and was vacuum filtered and the solid product was washed with acetone and then ether to obtain 2.3 g of the syn isomer of sodium 7-[{2-(2-amino-4-thiazolyl)-2-methoxyiminoacetyl}amino]-3-[(1-methyl-tetrazol-5-yl)-thiomethyl]-ceph-3-eme-4-carboxylate with a specific rotation $[\alpha]_D^{20} = -13.5° \pm 1°$ (c=1% in water). Na analysis: Calculated: 4.31%, Found: 4.8%.

EXAMPLE 21 syn isomer of sodium 3-acetylthiomethyl-7-[{2-(2-amino-4-thiazolyl)-2-methoxyiminoacetyl}amino]-ceph-3-eme-4-carboxylate A mixture of 4.5 g of the syn isomer of Example 6, 9 ml of ethanol and 9 ml of a molar aqueous sodium bicarbonate solution was stirred at room temperature for 5 minutes and was vacuum filtered. The filter was rinsed with a 1-1 water-methanol mixture and 110 ml of ethanol were added to the filtrate with stirring whereby the sodium salt crystallized. The mixture was diluted with 220 ml of ether, was stirred and vacuum filtered. The solid product was washed with a 1-1 ethanol-ether mixture and then with ether and was dried. The product was then dissolved in 40 ml of water and the pH of the solution was adjusted to 6.8–7 by addition of a few drops of acetic acid. The mixture was diluted with 100 ml of ethanol and the solvents were evaporated under reduced pressure at a temperature less than 35° C. The concentrate was effloresced twice with 50 ml of ethanol and was evaporated to dryness. The residue was dissolved in 15 ml of methanol and the solution was filtered. The filtrate was diluted with 150 ml of acetone whereby the sodium salt crystallized and the mixture was stirred for 5 minutes and was vacuum filtered. The solids were washed with acetone and then with ether and dried under reduced pressure to obtain 1.8 g of the syn isomer of sodium 3-acetylthiomethyl-7-[{2-(2-amino-4-thiazolyl)-2-methoxyiminoacetyl}amino]-ceph-3-eme-4-carboxylate with a specific rotation $[\alpha]_D^{20} = -31° \pm 2°$ (c=0.6% in water). Sodium analysis: Calculated: 4.65%, Found: 4.9%.

| Ultra violet Spectrum (ethanol) | | |
|---|---|---|
| max. at 235 nm | $E_1^1$ = 419 | |
| Inflex. towards 260 nm | $E_1^1$ = 343 | |
| Inflex. towards 300 nm | $E_1^1$ = 122 | |
| (ethanol-N/10 hydrochloric acid): | | |
| Inflex. towards 230 nm | $E_1^1$ = 280 | |
| max. at 263 nm | $E_1^1$ = 391 | $\epsilon$ = 19,700 |

EXAMPLE 22 syn isomer of microcrystalline sodium 3-acetylthiomethyl-7-[{2-(2-amino-4-thiazolyl)-2-methoxyiminoacetyl}amino]-ceph-3-eme-4-carboxylate A mixture of 471.5 mg of the syn isomer of Example 6 and 1.5 ml of a molar solution of anhydrous sodium acetate in anhydrous methanol was stirred and then 0.5 ml of ethanol were added thereto. The mixture was vacuum filtered and 2 ml of ethanol were added to the filtrate whereby the sodium salt crystallized. The mixture was vacuum filtered and the product was washed with methanol and then dried in an oven at 45° C. under reduced pressure to obtain 0.25 g of non-hydroscopic syn isomer of microcrystalline sodium 3-acetylthiomethyl-7-[{2-(2-amino-4-tetrazolyl)-2-methoxyiminoacetyl}amino]-ceph-3-eme-4-carboxylate. Sodium analysis: Calculated: 4.66%; Found: 4.6%.

EXAMPLE 23 syn isomer of 3-acetylthiomethyl-7-[{2-(2-amino-4-thiazolyl)-2-methoxyiminoacetyl}amino]-ceph-3-eme-4-carboxylic acid STEP A: syn isomer of ethyl 2-(2-chloroacetamido-4-thiazolyl)-2-methoxyiminoacetate A mixture of 45.8 g of ethyl 2-(2-amino-4-thiazolyl)-2-methoxyimino-acetate in 200 ml of methylene chloride was distilled to remove 20 ml of solvent for drying and the mixture was then cooled. 50 ml of pyridine and 41 g of monochloroacetic acid anhydride were added thereto and the mixture was slowly heated until dissolution. The mixture stood for 6 hours at 20° C. under nitrogen and after the addition of 5 ml of water, the mixture was stirred and poured into 300 ml of ice 2 N hydrochloric acid. The mixture was decanted and the aqueous phase was extracted with methylene chloride. The organic extracts were washed with water, with sodium bicarbonate solution and then water, were dried, passed through activated carbon and evaporated to dryness. The residue was added to 300 ml of isopropyl ether whereby crystallization occurred and the mixture was concentrated to obtain a thick paste. The mixture was iced and vacuum filtered and the solid was washed with isopropyl ether and dried to obtain 45.4 g of the syn isomer of ethyl 2-(2-chloroacetamido-4-thiazolyl)-2-methoxyiminoacetate melting at 113° C. A sample crystallized from a methylene chloride-isopropyl ether mixture melted at 118° C.

RMN Spectrum (CDCl3 60 MHz): (a) triplet centered about 1.38 ppm J=7 Hz; (b) singulet −4.05 ppm; (c) quadruplet centered about 4.44 ppm J=7 Hz; (d) singulet −4.33 ppm; (e) singulet −7.27 ppm; and (f) singulet −9.95 ppm

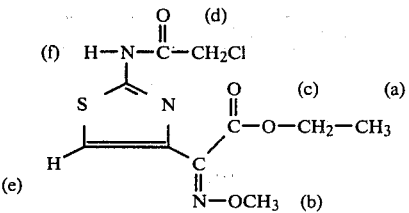

STEP B: syn isomer of 2-(2-chloroacetamido-4-thiazolyl)-2-methoxyiminoacetic acid 30 ml of pure sodium hydroxide solution were added at 20° C. under nitrogen to a mixture of 46 g of the product of Step A and 230 ml of absolute ethanol and as the product dissolved, the sodium salt crystallized until the medium become a mass. After 16 hours, the mixture was vacuum filtered and was washed. The sodium salt was dissolved in water and after icing the solution, 100 ml of 2 N hydrochloric acid were added thereto. The mixture was saturated with sodium chloride and was extracted with ethyl acetate containing 10% of ethanol. The organic extracts were dried, passed through carbon black and distilled under reduced pressure. The water was entrained with benzene and the residue was taken up in methylene chloride. The solution was distilled to dryness and the residue was again taken up in methylene chloride. The solution was iced and vacuum filtered. The solids were washed and dried to obtain 34.5 g of the syn isomer of 2-(2-chloroacetamido-4-thiazolyl)-2-methoxyiminoacetic acid melting about 200° C. The product was purified by crystallization from an acetone-isopropyl ether mixture.

Analysis: C8H8O4N3ClS; Molecular weight=277.68. Calculated: %C, 34.60; %H, 2.90; %N, 15.13; %Cl, 12.77; %S, 11.55. Found: %C, 34.8; %H, 2.8; %N, 14.8; %Cl, 12.6; %S, 11.5.

RMN Spectrum (DMSO 60 MHz): (a) singulet −3.92 ppm; (b) singulet −4.38 ppm (c) singulet about 5 ppm; (d) singulet −7.58 ppm; and (e) singulet −12.6 ppm.

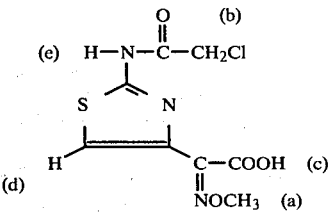

STEP C: syn isomer of 3-acetylthiomethyl-7-[{2-(2-chloroacetamido-4-thiazolyl)-2-methoxyiminoacetyl}amino]-ceph-3-eme-4-carboxylic acid 3.8 ml of thionyl chloride and 26 ml of methylene chloride were added at 0° C. under nitrogen to a mixture of 15.3 g of the syn isomer of 2-(2-chloroacetamido-4-thiazolyl)-2-methoxyiminoacetic acid in 80 ml of methylene chloride and after standing at 0° C. for 15 minutes, 7 ml of triethylamine were added thereto. A mixture of 14.4 g of 7-amino-3-acetylthiomethyl-ceph-3-eme-4-carboxylic acid in 100 ml of methylene chloride and 14 ml of triethylamine were added to the mixture at 0° C. under nitrogen and the temperature was allowed to return to 20° C. The mixture was stirred for an hour and was then evaporated to dryness at 30°–35° C. under reduced pressure. The residue was taken up in 250 ml of water and the solution was raised through carbon black. 50 ml of 2 N hydrochloric acid were added thereto and the mixture was vacuum filtered. The product was washed with water and the raw product was suspended in 80 ml of ethanol. 7 ml of triethylamine were added thereto at 5° C. and 15 ml of 4 N sulfuric acid were added thereto all at once with stirring at 5° C. After standing for 15 minutes, the mixture was vacuum filtered and the product was empasted with ethanol, then with ether and was dried under reduced pressure to obtain the syn isomer of 3-acetylthiomethyl-7-[{2-(2-chloroacetamido-4-thiazolyl)-2-methoxyiminoacetyl}-amino]-ceph-3-eme-4-carboxylic acid.

STEP D: syn isomer of 3-acetylthiomethyl-7-[{2-(2-amino-4-thiazolyl)-2-methoxyiminoacetyl}amino]-ceph-3-eme-4-carboxylic acid 1 g of potassium bicarbonate was added at 20° C. to a suspension of 5.48 g of the product of Step C in 10.6 ml of water and 912 mg of thiourea and after dissolution, the solution was stirred at 20° C. under nitrogen for 6 hours. The gummy precipitate started forming after 1½ hours and then 30 ml of water and 3 ml of formic acid were added thereto. After cooling to 5° C., the mixture was vacuum filtered and the filter was washed with water containing 10% of formic acid. The residue was dissolved towards 5° C. in 30 ml of water containing triethylamine and then 3 ml of formic acid were added at 5° C. The mixture was vacuum filtered and the solid was empasted with water containing formic acid. The brown gum formed was removed and the combined aqueous phases were passed through carbon black to form a clear yellow solution. The solution was saturated with ammonium sulfate and was vacuum filtered. The precipitate was empasted with water and was vacuum filtered and washed with water to obtain precipitate A. The mother liquors were saturated with ammonium sulfate and the mixture was vacuum filtered. The solid was washed 3 times with water to obtain precipitate B. Precipitates A and B were combined and taken up in ethanol. The mixture was stirred for an hour at 20° C. and then stood at 0° C. for 16 hours. The mixture was vacuum filtered and the solid was washed with ethanol, with ether and dried under reduced pressure to obtained the syn isomer of 3-acetylthiomethyl-7-[{2-(2-amino-4-thiazolyl)-2-methoxyiminoacetyl{amino]-ceph-3-eme-4-carboxylic acid identical to the products of Examples 6 and 18.

EXAMPLE 24

Injectable suspensions were prepared with 500 mg of either 7-[{2-(2-amino-4-thiazolyl)-2-methoxyiminoacetyl}amino]-3-[(1-methyl-tetrazol-5-yl)-thiomethyl]-ceph-3-eme-4-carboxylic acid or 3-acetylthiomethyl-7-[{2-(2-amino-4-thiazolyl)-2-methoxyiminoacetyl}amino]-ceph-3-eme-4-carboxylic acid or sodium 3-acetylthiomethyl-7-[{2-(2-amino-4-thiazolyl)-2-methoxyiminoacetyl}amino]-ceph-3-eme-4-carboxylate and sufficient sterile aqueous excipient to obtain a final volume of 5 ml.

EXAMPLE 25

Gelules were prepared containing 250 mg of either 7-[{2-(2-amino-4-thiazolyl)-2-methoxyiminoacetyl-{amino]-3-[(1-methyl-tetrazol-5-yl)-thiomethyl]-ceph-3-eme-4-carboxylic acid or 3-acetylthiomethyl-3-[{2-(2-amino-4-thiazolyl)-4-methoxyiminoacetyl}amino]-ceph-3-eme-4-carboxylic acid and sufficient excipient to obtain a final gelule of 400 mg.

PHARMACOLOGICAL DATA

A. In Vitro Activity

The method used was a dilution of a liquid medium where a series of tubes received the same quantity of a sterile nutritive media and increasing doses of the test compounds were placed therein. Then each tube was seeded with a bacterial strain and was incubated for 24 or 48 hours at 37° C. in an oven. The increasing inhibition was determined by transillumination to determine the minimum inhibiting concentration (MIC in μg/ml) and the results are reported in the following Tables.

| Product of Example 2 | MIC in μg/ml | |
|---|---|---|
| Strains | 24 H | 48 H |
| Staphylococcus aureus ATCC 6 538 Pen-Sensible | 1 | 1 |
| Staphylococcus aureus UC 1 128 Pen-Resistant | 2 | 2 |
| Staphylococcus aureus exp. n° 54 146 | 2 | 2 |
| Streptococcus pyogenes A 561 | ≦0,02 | ≦0,02 |
| Streptococcus faecalis 5 432 | 1 | 2 |
| Streptococcus faecalis 99 F 74 | 2 | 5 |
| Bacillus subtilis ATCC 6 633 | 0,6 | 1 |
| Escherichia Coli Sensible Tetracycline ATCC 9 637 | 0,6 | 0,6 |
| Escherichia Coli Resistant Tetracycline ATCC 11 303 | 0,1 | 0,2 |
| Escherichia Coli Exp. TO$_{26}$B$_6$ | 0,4 | 0,4 |
| Escherichia Coli Resistant Gentamicine, Tobramycine R 55 123 D | 0,4 | 0,4 |
| Klebsiella pneumoniae Exp. 52 145 | 0,05 | 0,1 |
| Klebsiella pneumoniae 2 536 Resistant Gentamycine | 0,6 | 1 |
| Proteus mirabilis (indol—) A 235 | 0,2 | 0,2 |
| Salmonella typhimurium 420 | 0,6 | 0,6 |
| Enterobacter cloacae 681 | 40 | 40 |
| Providencia Du 48 | 2 | 5 |
| Serratia Resistant Gentamicine 2 532 | 1 | 1 |

| Product of Example 4 | MIC in μg/ml | |
|---|---|---|
| Strains | 24 H | 48 H |
| Staphylococcus aureus ATCC 5 638 Pen-Sensible | 1 | 1 |
| Staphylococcus aureus UC 1 128 Pen-Resistant | 2 | 2 |
| Staphylococcus aureus exp. n° 54 146 | 2 | 2 |
| Streptococcus pyogenes A 561 | ≦0,02 | ≦0,02 |
| Streptococcus faecalis 5 432 | 2 | 2 |
| Streptococcus faecalis 99 F 74 | 2 | 10 |

-continued

| Product of Example 4 | | |
|---|---|---|
| | MIC in µg/ml | |
| Strains | 24 H | 48 H |
| Bacillus subtilis ATCC 6 633 | 2 | 5 |
| Escherichia Coli Sensible Tetracycline ATCC 9 637 | 0,4 | 0,4 |
| Escherichia Coli Resistant Tetracycline ATCC 11 303 | 0,05 | 0,05 |
| Escherichia Coli Exp. TO$_{26}$B$_6$ | 0,2 | 0,2 |
| Escherichia Coli Resistant Gentamicine, Tobramycine R 55 123 D | 0,2 | 0,2 |
| Klebsiella pneumoniae Exp. 52 145 | 0,02 | 0,02 |
| Klebsiella pneumoniae 2 536 Resistant Gentamicine | 0,4 | 0,6 |
| Proteus mirabilis (indol−) A 235 | 0,05 | 0,05 |
| Proteus vulgaris (indol+) A 232 | 3 | 20 |
| Salmonella typhimurium 420 | 0,2 | 0,2 |
| Enterobacter cloacae 681 | 20 | 20 |
| Providencia Du 48 | 2 | 2 |
| Pseudomonas 3 935 Exp. SG | 20 | 40 |
| Serratia Resistant Gentamicine 2 532 | 1 | 1 |

| Product of Example 21 | | |
|---|---|---|
| | MIC in µg/ml | |
| Strain | 24 H | 48 H |
| Golden Staphylococcus 68 666 | 3 | 5 |
| Escherichia Coli 73 316 | 0.2 | 0.2 |
| Escherichia Coli 72 806 | 1 | 1 |
| Escherichia Coli 69 916 | 0.4 | 0.4 |
| Escherichia Coli 69 886 | 0.6 | 1 |
| Escherichia Coli 68 696 | 0.4 | 0.4 |
| Escherichia Coli 68 956 | 0.4 | 0.4 |
| Escherichia Coli 21 976 | 0.6 | 0.6 |
| Escherichia Coli 19 976 | 0.6 | 0.6 |

B. Experimental Infection with Escherichia Coli (T) O$_{26}$B$_6$

The products of Example 6 and 10 were studied for their activity against an experimental infection of Escherichia Coli in groups of 10 male mice weighing about 22 g. The mice received an intraperitoneal injection of 0.5

| | Product of Example 6 MIC in µg/ml | | Product of Example 17 MIC in µg/ml | | Product of Example 10 MIC in µg/ml | | Product of Example 15 MIC in µg/ml | |
|---|---|---|---|---|---|---|---|---|
| Strains | 24 H | 48 H | 24 H | 48 H | 24 H | 48 H | 24 H | 48 H |
| Staphylococcus aureus ATCC 6 538 Pen-Sensible | 2 | 2 | 20 | 20 | 20 | 40 | >100 | >100 |
| Staphylococcus aureus UC 1 128 Pen-Resistant | 5 | 5 | 40 | 100 | 40 | 40 | >100 | >100 |
| Staphylococcus aureus exp. n° 54 146 | 2 | 2 | 40 | 40 | 40 | 40 | >100 | >100 |
| Streptococcus pyogenes A 561 | ≦0.02 | ≦0.02 | 0.2 | 0.2 | 0.05 | 0.05 | 2 | 3 |
| Streptococcus faecalis 5 432 | 5 | 5 | >100 | >100 | 20 | >40 | >100 | >100 |
| Streptococcus faecalis 99 F 74 | 5 | >40 | >100 | >100 | 20 | >40 | >100 | >100 |
| Bacillus subtilis ATCC 6 633 | 1 | 2 | 5 | 20 | 20 | >40 | >100 | >100 |
| Escherichia Coli Sensible Tetracycline ATCC 9 637 | 0.6 | 0.6 | 40 | 40 | 0.6 | 0.6 | >100 | >100 |
| Escherichia Coli Resistant Tetracycline ATCC 11 303 | 0.1 | 0.1 | 5 | 5 | 0.2 | 0.2 | >100 | >100 |
| Escherichia Coli Exp. TO$_{26}$B$_6$ | 0.4 | 0.4 | 20 | 40 | 0.4 | 0.6 | >100 | >100 |
| Escherichia Coli Resistant Gentamicine, Tobramycine R 55 123 D | 0.6 | 0.6 | 40 | 40 | 0.6 | 0.6 | >100 | >100 |
| Klebsiella pneumoniae Exp. 52 145 | 0.1 | 0.1 | 40 | 40 | 0.1 | 0.1 | 100 | 100 |
| Klebsiella pneumoniae 2 536 Resistant Gentamicine | 1 | 2 | >100 | >100 | 0.6 | 2 | >100 | >100 |
| Proteus mirabilis (indol−) A 235 | 0.05 | 0.1 | 5 | 40 | 0.1 | 0.2 | 20 | 40 |
| Proteus vulgaris (indol+) A 232 | 5 | 10 | >100 | >100 | 3 | 20 | >100 | >100 |
| Salmonella typhimurium 420 | 0.4 | 0.4 | 40 | 40 | 0.6 | 0.6 | >100 | >100 |
| Enterobacter cloacae 681 | 10 | 20 | 40 | 100 | | | | |
| Providencia Du 48 | 10 | 10 | >100 | >100 | 2 | 5 | >100 | >100 |
| Serratia Resistant Gentamicine 2 532 | 1 | 2 | >100 | >100 | 5 | 10 | >100 | >100 |

| Product of Example 21 | | |
|---|---|---|
| | MIC in µg/ml | |
| Strain | 24 H | 48 H |
| Pathogenic white Staphylococcus 69 396 | 2 | 2 |
| White Staphylococcus 21 976 | 3 | 5 | ml of a 24 hour old culture in a nutritive media of Escherichia Coli (T) O$_{26}$B$_6$ of the Pasteur Institute diluted 1/5.5 with distilled water. The test product was administered subcutaneously or orally 1 hour and 5 and 24 hours after the infection and the number of dead was determined during 8 days. The results are reported in the following Table.

| | admin- istration | Morality After | | | | | | | | | | Mice surviving on the 8th day |
|---|---|---|---|---|---|---|---|---|---|---|---|---|
| | | 21 H 30 | 24 H | 24 H 30 | 25 H 30 | 28 H | 47 H | 54 H | 70 H | 5 J | 6 J | |
| Controls | s. c. | 10 | | | | | | | | | | 0/10 |
| Product of example 6 3 × 0,05 mg | s. c. | 4 | | | | | | 1 | | 1 | | 4/10 |
| Product of example 6 3 × 0,1 mg | s. c. | 1 | 1 | | 1 | | | | | 2 | | 5/10 |
| Product of example 6 3 × 0,2 mg | s. c. | 1 | | | | | | 1 | | 1 | | 7/10 |

Various modification of the products and processes of the invention may be made without departing from the spirit or scope thereof and it should be understood that the invention is to be limited only as defined in the appended claims.

We claim:

1. A compound of the formula

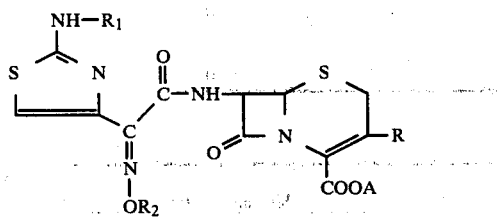

wherein R is selected from the group consisting of alkyl of 1 to 5 carbon atoms and cycloalkyl of 3 to 5 carbon atoms, $R_1$ is hydrogen, $R_2$ is selected from the group consisting of 1 to 4 carbon atoms and alkenyl and alkynyl of 2 to 4 carbon atoms, A is selected from the group consisting of hydrogen, an alkali metal cation, or equivalent of an alkaline earth metal or magnesium and an organic amine base cation and $OR_2$ is in the syn position.

2. A compound of claim 1 wherein $R_2$ is methyl, A is hydrogen and R is selected from the group consisting of methyl and isopropyl.

3. A compound of claim 1 which is syn isomer of 7-[{2-(2-amino-4-thiazolyl)-2-methoxyiminoacetyl}-amino]-3-isopropyl-ceph-3-eme-4-carboxylic acid.

4. A compound of claim 1 which is syn isomer of 7-[{2-(2-amino-4-thiazolyl)-2-methoxyiminoacetyl}-amino]-3-methyl-ceph-3-eme-4-carboxylic acid.

5. An antibiotic composition comprising an antibiotically effective amount of at least one compound of claim 1 and an inert pharmaceutical carrier.

6. A method of treating bacterial infections in warm-blooded animals comprising administering to warm-blooded animals an antibiotically effective amount of at least one compound of claim 1.

7. The method of claim 6 wherein the compound is syn isomer of 7-[{2-(2-amino-4-thiazolyl)-2-methoxyiminoacetyl}amino]-3-isopropyl-ceph-3-eme-4-carboxylic acid.

8. The method of claim 6 wherein the compound of syn isomer of 7-[{2-(2-amino-4-thiazolyl)-2-methoxyiminoacetyl}amino]-3-methyl-ceph-3-eme-4-carboxylic acid.

* * * * *

UNITED STATES PATENT AND TRADEMARK OFFICE
CERTIFICATE OF CORRECTION

PATENT NO. : 4,396,618                  Page 1 of 2

DATED : August 2, 1983

INVENTOR(S) : RENE HEYMES ET AL.

It is certified that error appears in the above-identified patent and that said Letters Patent is hereby corrected as shown below:

Column 3, line 16, 19, 25, 31, 33, 41, 44, 50; Column 8, lines 52, 54, 59; Column 12, lines 4, 62; Column 13, line 5; Column 14, line 4, 57; Column 15, lines 10, 23, 49; Column 16, lines 14, 31, 36, 61; Column 17, lines 48, and 58; Column 18, lines 14, 54; Column 19, lines 32 and 46; Column 20, line 42; Column 21, line 26; Column 22, line 42; Column 32, line 2 of claims 7 and 8: "methox-" should be -- methoxy- --.

Column 3, lines 17, 20, 26, 32, 34, 42, 45, 51; Column 8, lines 53, 55, 60; Column 12, lines 5, 63; Column 13, line 6; Column 14, line 5; Column 16, line 62 Column 17, lines 49, 59; Column 18, line 15; Column 19, lines 33, 47; Column 20, line 43; Column 21, line 27; Column 22, line 43; Column 32, line 3 of claims 7 and 8: "yiminoacetyl" should be -- aminoacetyl --.

Column 2, line 65; Column 8, line 25: "CH-" should be -- $CH_2$- --.

Column 2, line 66; Column 8, line 26: Delete "$_2$-".

Column 3, lines 26, 45; Column 11, line 8; Column 13, line 6; Column 16, line 62; Column 22, line 43: "thi-" should be -- thio- --.

Column 3, line 27, 46, 50; Column 11, line 9; Column 13, line 7; Column 16, line 63; Column 22, line 44; Column 23, line 37; Column 26, line 7: "omethyl" should be -- methyl --.

UNITED STATES PATENT AND TRADEMARK OFFICE
CERTIFICATE OF CORRECTION

PATENT NO. : 4,396,618  Page 2 of 2
DATED : August 3, 1983
INVENTOR(S) : RENE HEYMES ET AL.

It is certified that error appears in the above-identified patent and that said Letters Patent is hereby corrected as shown below:

Column 3, line 49; Column 23, line 36; Column 26, line 6:
    "acetylthi-" should be -- acetylthio- --.
Column 13, line 7: "cephem" should be -- ceph --.
Column 14, line 8; Column 15, lines 11, 24, 50; Column 16,
    lines 15, 32, 37; Column 18, line 55:
    "yimino" should be -- imino --.
Column 17, line 57; Column 21, line 25:
    "acetox-" should be -- acetoxy- --.
Column 17, line 58; Column 21, line 26:
    "ymethyl" should be -- methyl --.
Column 21, line 39: "eas" should be -- was --.
Column 24, line 24: "methoxyiminoa-" should be
    -- methoxyimino- --.
Column 24, line 25: "cetic acid" should be -- acetic acid --.
Column 30, line 20: "Contrcls  2  1  7  3 ..." should be -- Controls
    2  1  1  3 ... --.

Signed and Sealed this

First Day of May 1984

[SEAL]

Attest:

GERALD J. MOSSINGHOFF

Attesting Officer   Commissioner of Patents and Trademarks